United States Patent [19]

Gray et al.

[11] 4,073,620
[45] Feb. 14, 1978

[54] BINDER-SUBSTRATE ANALYZER

[75] Inventors: Michael James Gray, San Francisco; Raymond E. Stanton, Alameda, both of Calif.

[73] Assignee: Gray and Stanton, San Francisco, Calif.

[21] Appl. No.: 756,311

[22] Filed: Jan. 3, 1977

[51] Int. Cl.² .............................................. G01N 31/06
[52] U.S. Cl. ..................................... 23/253 R; 23/259
[58] Field of Search ............................. 23/253 R, 259

[56] References Cited

U.S. PATENT DOCUMENTS

| 3,488,156 | 1/1970 | Good et al. | 23/253 R |
| 3,525,591 | 8/1970 | Jungner et al. | 23/253 R |
| 3,622,279 | 11/1971 | Moran | 23/253 R |

*Primary Examiner*—Robert M. Reese
*Attorney, Agent, or Firm*—Townsend and Townsend

[57] ABSTRACT

Apparatus for performing binder-substrate processing of clinical substances is disclosed. An operating head is provided which includes an array of upwardly opening receptacles each having a closed bottom. A temperature control element is located in the operating head proximate the receptacles. The operating head also includes a manifold having an influx chamber, an efflux chamber and a plurality of hollow prongs emanating from the influx chamber and through the efflux chamber. The prongs extend downwardly into respective of the receptacles to provide fluid communication between the influx chamber and the interior of the receptacles through the prongs. The efflux chamber is in fluid communication with the open ends of the receptacles to drain fluid therefrom. A solid phase binder is located in the bottoms of the respective receptacles, and may be coated on solid phase elements located in the receptacles or on the receptacles themselves. The solid phase binder is immersed in the clinical substances for incubation by the temperature control element. After incubation of the clinical substances, the operating head is inverted. A washing fluid is injected into the influx chamber of the inverted operating head so that the washing fluid flows upwardly through the prongs to wash excess of the clinical substances from the solid phase binder retained in the receptacles. The washing fluid is drained from the operating head through the efflux chamber. A drying fluid is usually injected into the influx chamber of the inverted operating head so that the drying fluid flows upwardly through the prongs and into the receptacles to dry the solid phase binder and incubated clinical substances adhering thereto.

13 Claims, 9 Drawing Figures

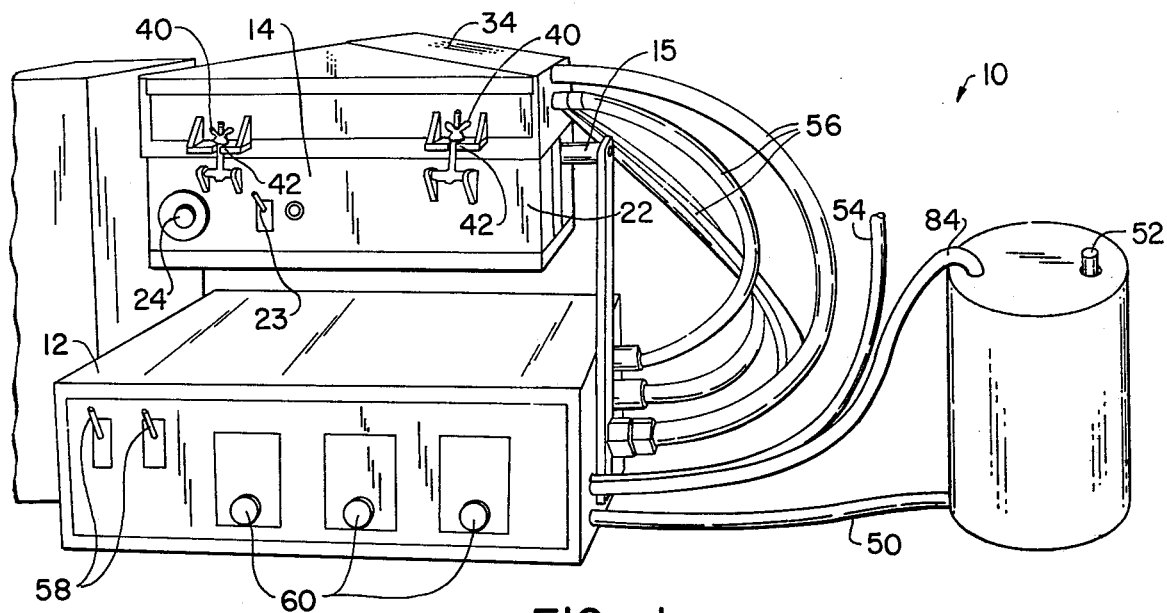
FIG._1.
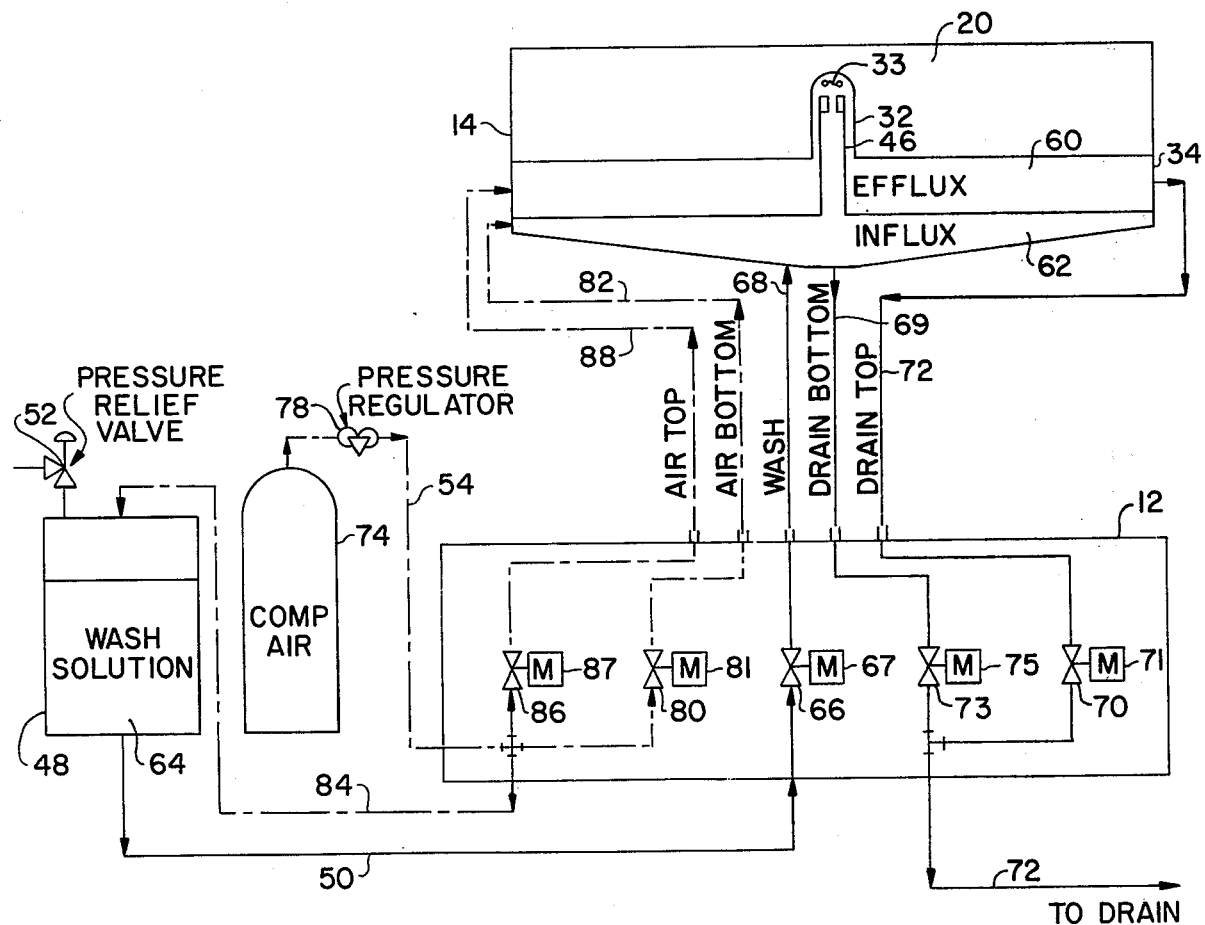
FIG._3.

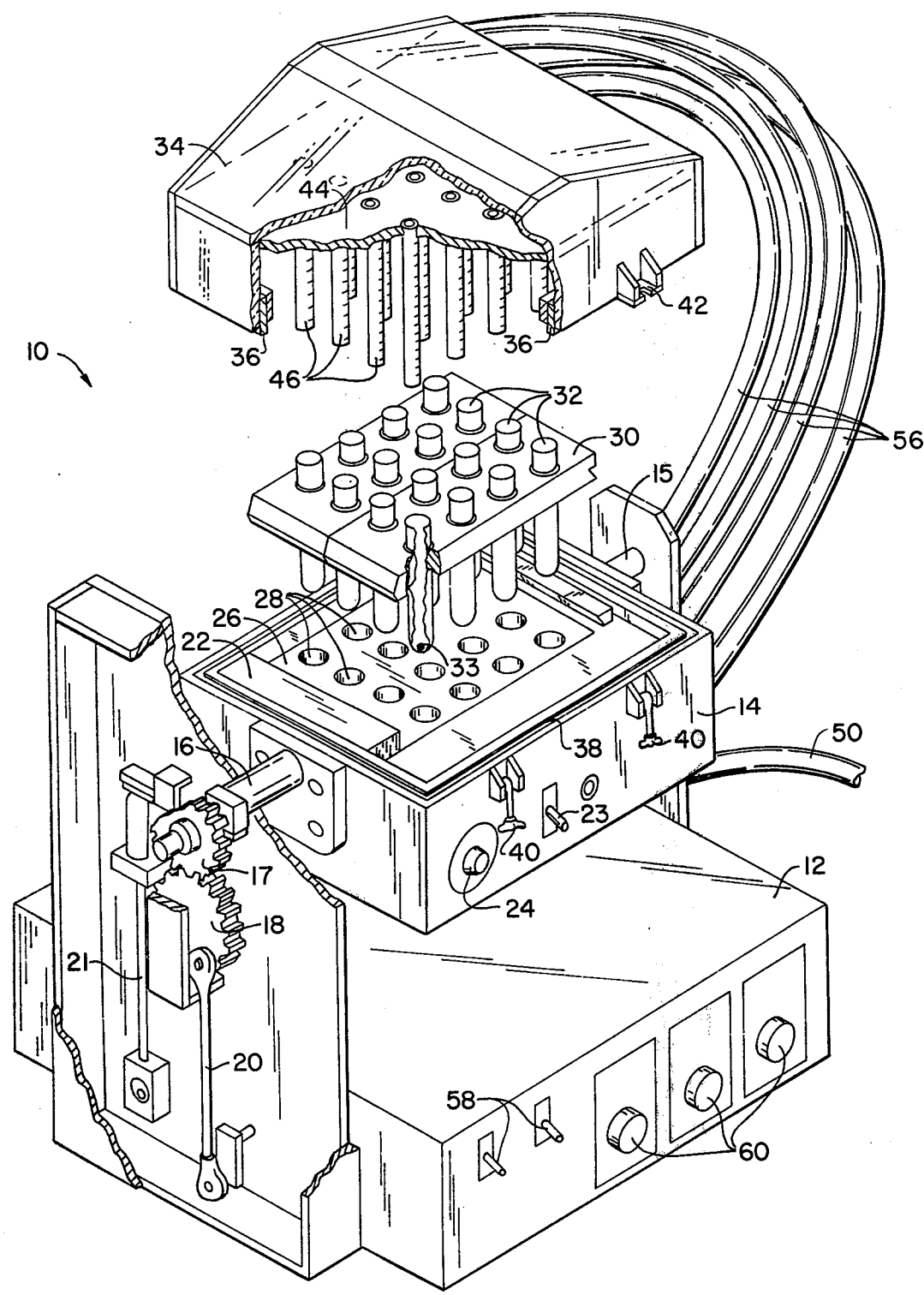
FIG._2.

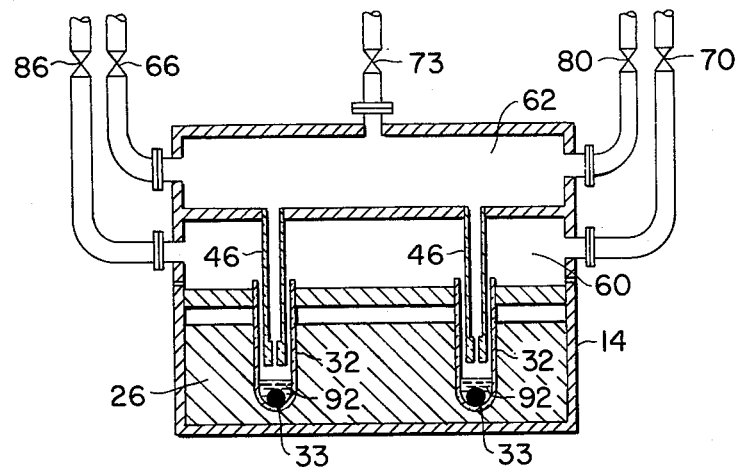
FIG._4A.
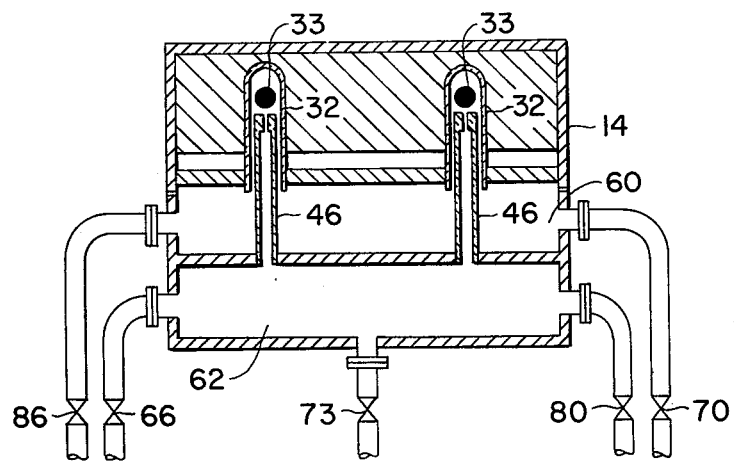
FIG._4B.
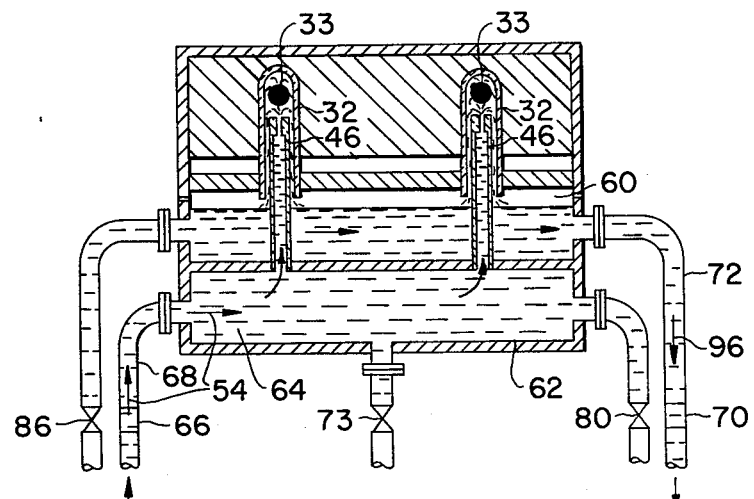
FIG._4C.

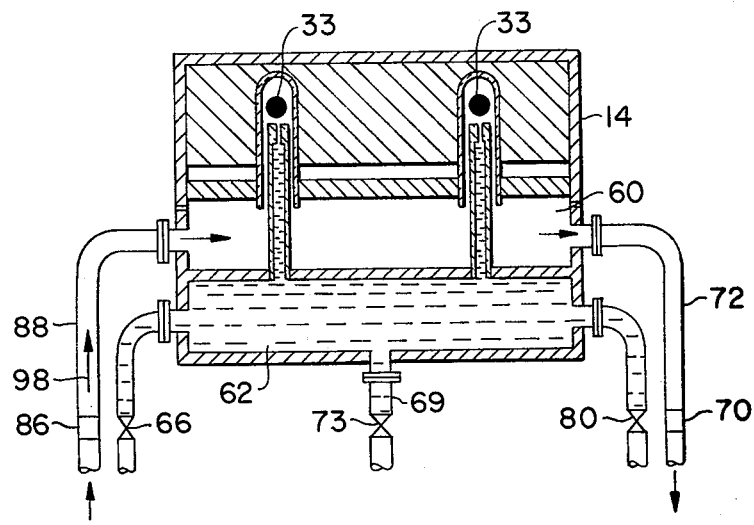
FIG._4D.
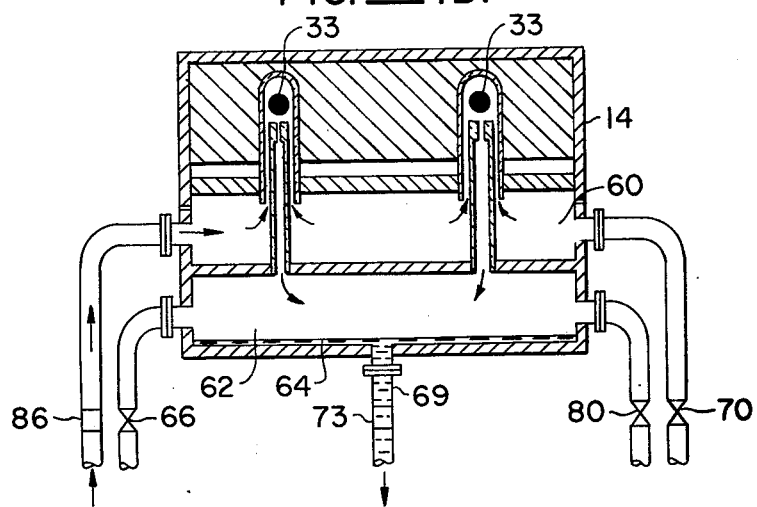
FIG._4E.
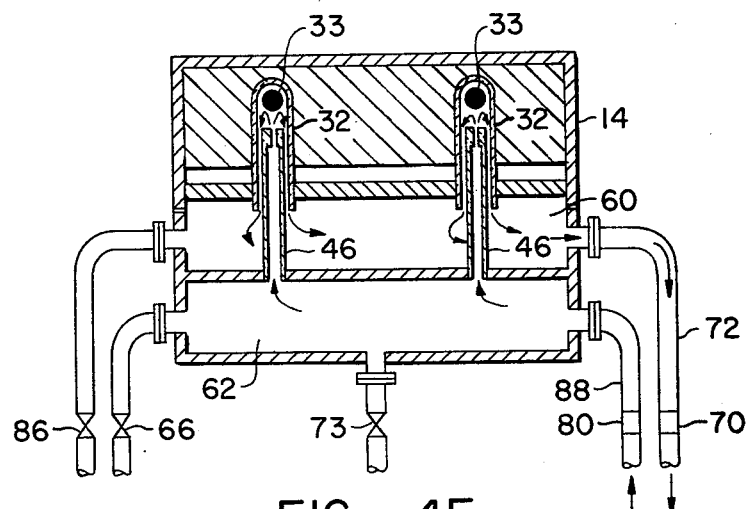
FIG._4F.

BINDER-SUBSTRATE ANALYZER

BACKGROUND OF THE INVENTION

The present invention relates to apparatus for performing the incubation and washing requirements of solid-phase, binder-substrate analysis of clinical substances.

A larger number of different types of tests are performed on various clinical substances such as human serum by using binder-substrate analysis. In such an analysis, a binding agent is typically suspended in a suppportive medium to which might be added either a quantitated standard substrate or the unquantitated substrate in the clinical substance. Additionally, a measure of labeled substrate, as nearly identical to the substrate of the standard and clinical substance as possible, is added to the medium to serve as a marker for the distribution of all substrate during incubation. This supportive medium is then incubated under precisely controlled conditions favoring the equilibrium of binder-substrate complex and the individual components. After the incubation has achieved a point of equilibrium, some method of separation is performed allowing isolation of either the binder-substrate complex or the free components.

Since the labeled substrate is selected for those pertinent similarities to the standard and unquantitated substrate, it will distribute itself exactly like those unlabeled substrates at equilibrium. Measurement by suitable means of that label in the isolated fraction will provide the same results as if the total (labeled and unlabeled) substrate in the isolated fraction is measured. Comparison of the amount of substrate found in the isolate of the unquantitated clinical substances to that of the standards provides the result of the analysis.

One such method of separation, isolating the binder-substrate complex from the components, is termed "solid phase". Solid phase defines the physical condition of the binder-substrate complex at the point of equilibrium when the separation step is to occur. Typically, the binder is originally the solid phase component. When incubation is terminated, the separation step involves isolation of the solid phase binder-substrate complex from the liquid phase of the assay medium. If the binder is physically attached to microscopic-solid particles, the separation would involve a centrifuge. If the binder is attached to a large enough particle such as a ¼ inch dia. sphere or the bottom interior surface of a test tube, the separation step involves decantation or aspiration of the liquid phase from the immobilized, solid-phase binder-substrate complex.

The application of solid phase to the binder-substrate analysis has eliminated the centrifuge in several cases (where large enough supports are used); but added to the procedure, time and/or temperature enhancement of the incubation step, and a wash step(s) to adequately isolate the solid phase complex from the liquid phase components. These additional requirements must be controlled to guarantee reproducibility between all specimens.

One such application of solid-phase binder-substrate analysis determines the presence of hepatitis virus in serum specimen. The primary binder is an antibody to hepatitis virus, attached to a ¼ inch dia. bead. This solid-phase binder is immersed in a buffered medium containing a measure of specimen, all contained within a test tube.

The test tube is maintained at a controlled temperature for sufficient time (incubation) to allow optimum formation of the antibody-virus complex on the surface of the plastic bead. The liquid medium containing all unreacted substances is then removed from the test tube and the bead and inner surfaces of the test tube are adequately washed leaving the solid phase antibody-virus complex. A second antibody, similar in binding properties to the primary but solubilized in a buffered medium, is then added to the test tube containing the solid phase complex. Additionally the second antibody is suitably labeled to allow subsequent detection. The test tube is again maintained according to those parameters optimizing the formation of a second binding; the virus by the labeled antibody. The only virus available to this second, labeled antibody is carried over through the washing(s) from the first incubation. Therefore, any secondary binding will join the labeled antibody to the solid-phase antibody-virus complex forming a sandwich. The liquid medium containing all unreacted substances is again removed from the test tube and the bead and inner surfaces of the test tube are washed leaving the solid-phase primary antibody-virus-labeled antibody complex. The plastic bead is then transfered to a carrier-tube suitable to the label detection apparatus. Detection of label on the plastic bead implies presence of virus since no other form of labeled antibody is carried over through the washing(s) from the second incubation.

At present, the incubations, washings and drying of the solid phase components in this variety of binder-substrate analysis are generally performed by hand. The test consumes a large amount of technician time, thus labor costs are relatively high. The large number of manual steps often cause errors in the testing procedures. Variations in the parameters of incubation time and temperature, and wash volumes, inherent in manual processing, produces nonuniformity in test results. A further problem presented by extensive manual manipulation is cross-contamination of the samples and the constant exposure of the technician to potential biological and radioactive hazards.

SUMMARY OF THE INVENTION

The present invention provides apparatus for performing binder-substrate processing of clinical substances. An operating head is provided which includes an array of upwardly opening receptacles each having a closed bottom. A temperature control element is located in the operating head proximate the receptacles. The operating head also includes a manifold having an influx chamber, an efflux chamber and a plurality of hollow prongs emanating from the influx chamber and through the efflux chamber. The prongs extend downwardly into respective of the receptacles to provide fluid communication between the influx chamber and the interior of the receptacles to the prongs. The efflux chamber is in fluid communication with the open ends of the receptacles to drain fluids therefrom. A solid phase binder is located in the bottoms of the respective receptacles, and may be coated on solid phase elements located in the receptacles or on the receptacles themselves. The solid phase binder is immersed in the clinical substances for incubation by the temperature control element. After incubation of the clinical substances, the operating head is inverted. A washing fluid is injected into the influx chamber of the inverted operating head so that the washing fluid flows upwardly through the prongs to wash excess of the clinical substances from the solid phase elements in the receptacles. The washing fluid is drained from the operating head through the efflux chamber. A drying fluid is often injected into the influx chamber of the inverted operating head so that the drying fluid flows upwardly through the prongs and into the receptacles to dry the solid phase elements and incubated clinical substances adhering thereto.

The present invention eliminates a large number of the manual steps which have been required in the past to perform binder-substrate processing. The time required of a laboratory technician to perform this type of analysis is substantially reduced, resulting in a corresponding reduction in labor costs. Furthermore, the analysis can be performed in a repeatable and consistent manner, giving greater uniformity in the results. The orientation and relative positioning of the test tubes during washing virtually eliminates the potential for cross-contamination of samples. The overall design of the unit allowing isolation of both liquids and vapors eliminates the hazards to the technician. In addition, a large number of individual samples can be processed at the same time, under virtually identical conditions, further increasing the efficiency of the system.

The novel features which are characteristic of the invention, as to organization and method of operation, together with further objects and advantages thereof will be better understood from the following description considered in connection with the accompanied drawings which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of the apparatus of the present invention;

FIG. 2 is an exploded view of the apparatus of FIG. 1;

FIG. 3 is a schematic view of the fluid control system of the present invention;

FIGS. 4A-4F is a sequence of schematic views illustrating the operation of the present invention.

DESCRIPTION OF THE PREFERRED EMBODIMENT

The construction of the preferred embodiment of the binder-substrate processor 10 of the present invention is illustrated primarily by way of reference to FIGS. 1 and 2. Processor 10 includes a control unit 12 having an operating head 14 superimposed thereabove. Operating head 14 is mounted on shafts 15, 16. Shaft 16 is driven by gears 17, 18 and inverting arm 20 to control the orientation of operating head 14. A rocker arm 21 also connects the shaft 16 to rock head 14 for purposes described below.

Operating head 14 includes a base 22 having an internal heating block 26 controlled by switch 23 and thermostat 24. A plurality of recesses 28 are formed in heating block 26. A rack 30 supporting a plurality of test tubes 32 is attachable to base 22 (see FIG. 2). When rack 30 is so attached, test tubes 32 extend downwardly into recesses 28 in heating block 26 so that the heating block surrounds the bottoms of the test tubes. A solid phase element such as bead 33 coated with a solid phase binder may be located at the bottom of each test tube 32. Alternatively, the solid phase binder may simply be coated on test tube 32 which then acts as the solid phase element or on a plurality of solid phase elements located in the test tubes.

A cover 34 fits over and attaches to base 22 to form the upper portion of the operating head. A rib 36 on the underside of cover 34 fits within a corresponding groove 38 to form a water tight seal between the cover 34 and base 22. Cover 34 is located in position by wing nut 40 which engages slots 42 projecting outwardly from cover 34 (see FIG. 1).

When cover 34 is fixed to base 22, a chamber is formed between a plate 44 within cover 34 and the upper portion of base 22, which acts as an efflux chamber. In addition, plate 44 defines a chamber within cover 34 which is designated the influx chamber. A plurality of hollow prongs 46 extend downwardly from plate 44 through the efflux chamber and into the interior of test tubes 32. Prongs 46 are in fluid communication with the influx chamber and confine each bead 33, if used, in the bottom of its respective test tube 32. The influx and efflux chambers together with prongs 46 provide a manifold system for operating head 14, as described in detail hereinafter.

A container 48 of washing fluid is connected with control unit 12 by tube 50. The washing fluid is maintained under pressure in container 48, and a relief valve 52 is provided to relieve excess pressure. Another tube 54 emanates from control unit 12 and connects with a source of pressurized air or another drying fluid (not shown in FIG. 1). A plurality of tubes 56 interconnect control unit 12 with operating head 14 as will be described in more detail hereinafter. Various switches 58 and timers 60 are provided to control the operation of processor 10.

The function of the various fluid connections in the analyzer of the present invention are illustrated in more detail by way of reference to the schematic view of FIG. 3. In FIG. 3, operating head 14 is illustrated in its inverted position, which is accomplished by rotating operating head 14 on shafts 15, 16 (see FIGS. 1 and 2). In this configuration, the base 20 of operating head 14 is located above cover 34. Each test tube 32 (only one test tube is illustrated for clarity) now opens downwardly, and each prong 46 projects upwardly into each respective test tube. Efflux chamber 60 is now superimposed over influx chamber 62. Operating head 14 is shown in its inverted configuration in FIG. 3 because all fluids are applied while the operating head is so inverted.

Container 48 of wash solution 64 is communicated to control unit 12 through tube 50. A valve 66 is located within the control box 12, and is operated by a solenoid 67 to control the flow of washing fluid to influx chamber 62 through tube 68. When valve 66 is open, washing fluid is injected into influx chamber 62, and passes upwardly through prong 46 into receptacle 32. At the same time, valve 73 is opened by solenoid 75 so that the washing fluid can drain out of efflux chamber 60 through tube 72 for safe disposal.

A source 74 of compressed air or other drying medium is connected to control unit 12 by tube 54. A pressure regulator 78 is located intermediate tube 54. A valve 80 actuated by solenoid 81 controls the flow of the compressed air under pressure to influx chamber 62 through tube 82. When the valve 80 is open, compressed air is injected into influx chamber 62, and passes upwardly through prong 46 and into receptacle 32.

Valve 70 is opened at the same time to allow air to escape through efflux chamber 60 and tube 72.

Compressed air 74 is also communicated to container 48 of wash solution 64 through tube 84 to maintain the wash solution under pressure. In addition, valve 86 may be opened by actuating solenoid 87 to communicate compressed air to efflux chamber 60 through tube 88 to blow the wash solution out of the chamber and prevent a vacuum from forming in the efflux chamber during certain draining operations.

An exemplary manner in which a binder-substrate processor is performed by processor 10 is illustrated by way of reference to the schematic views of FIGS. 4A–4F. In each of these figures, operating head 14 is illustrated schematically together with a pair of test tubes 32 and their associated apparatus. Valves 66, 70, 73, 80 and 86 correspond with valves denoted by the same numerals in FIG. 3.

Referring initially to FIG. 4A, operating head 14 is in its normal upright position, and test tubes 32 open upwardly. Beads 33 are located in the bottom of test tubes 32 as illustrated in FIG. 4A, and are immersed in a diluted sample 92. Typically, beads 33 are plastic and coated with a binder such as an antibody to a virus or other suspected constituent of sample 92. Often, beads 33 are not used and the binder is coated directly on the inside walls of test tubes 32. Heating block 26 is actuated to incubate sample 92 and generate reactions which may be possible between certain constituents of the diluted sample and the binder. Operating head 14 may be rocked back and forth on shafts 15, 16 using rocker arm 21 (see FIGS. 1 and 2) during the incubation period to facilitate any such reaction. During the incubation phase, all valves 66, 70, 73, 80 and 86 are generally closed.

After incubation, operating head 14 is inverted as illustrated in FIG. 4B by rotating it on shafts 15, 16 (see FIGS. 1 and 2). The dimensions of beads 33 are larger than the annular distance between prongs 46 and test tubes 32 so that the beads are confined within the test tubes. Excess diluted sample 92 which has not adhered to the binder on beads 33 is drained from test tubes 32. If the sought after virus was contained in the patient sample, a certain quantity thereof will be bound to the binder on beads 33.

The binder on beads 33 is then washed as illustrated by way of reference to FIG. 4C. Valve 66 is opened, and washing fluid 64 is injected into influx chamber 62 as illustrated by arrows 94. Washing fluid 64 passes upwardly through prongs 46 to wash the binder on beads 33 and the interior of test tubes 32. The washing fluid then drains through test tubes 32 along the outside of prongs 46 and into efflux chamber 60. Valve 70 is also open so that washing fluid 64 can drain from efflux chamber 60 through tube 72, as depicted by arrows 96.

After the wash cycle is completed, valve 66 is closed and valve 86 is opened as illustrated in FIG. 4D. Compressed air passes into efflux chamber 60 through tube 88 as depicted by arrow 98 to allow the wash solution to drain through tube 72.

After the wash fluid has been drained from efflux chamber 60, valve 73 is opened as depicted in FIG. 4E to allow the wash fluid in influx chamber 62 to be drained from the system through tube 69. Valve 70 may be closed during this operation but valve 86 remains open to blow out the remaining wash solution and to prevent a vacuum from forming in the system.

After all of the wash solution has been drained from operating head 14, the binder on beads 33 and any clinical substances bound thereto are dried as illustrated in FIG. 4F. Valve 86 is closed, and compressed air or another drying medium is injected into influx chamber 62 through tube 88 by opening valve 80. The compressed air passes upwardly through prongs 46 to completely dry beads 33 and substances bound thereto and the interior of test tubes 32. The drying air passes out of test tubes 32 into efflux chamber 60 and out of operating head 14 through tube 72.

To operate substrate analyzer 10, test tubes 32 containing a binder coated to the interior of the test tubes or to a plurality of beads 33 located in the individual test tubes are placed in rack 30. Various dilute samples to be tested are then dispensed into respective test tubes, and rack 30 is mounted to the base 22 of operating head 14. Cover 34 is then placed over the operating head and secured thereto.

The parameters of the incubation, wash, and dry cycles are set as desired on processor 10 using the various dials 24 and 60 provided for that purpose. Processor 10 is then actuated, and automatically performs the incubation, wash, and dry cycles as preselected. After the cycles have been completed, it may be desirable for certain types of tests to add a second clinical substance to the various test tubes and the entire process can be repeated to perform the second phase of such tests.

While a preferred embodiment of the present invention has been illustrated in detail, it is apparent that modifications and adaptations of that embodiment will occur to those skilled in the art. However, it is to be expressly understood that such modifications and adaptations are within the spirit and scope of the present invention, as set forth in the following claims:

What is claimed is:

1. Apparatus for performing binder-substrate processing of clinical substances comprising:
    an operating head which includes an array of generally upwardly opening receptacles each having a closed bottom, temperature control means proximate the closed bottom of the receptacles, and a manifold having an influx chamber, an efflux chamber and a plurality of hollow prongs emanating from the influx chamber through the efflux chamber and downwardly into respective of the receptacles to provide fluid communication between the influx chamber and the interior of the receptacles through the prongs, said efflux chamber being in fluid communication with the open ends of the receptacles;
    a solid phase binder located at the bottoms of the respective receptacles, said solid phase binder being immersed in said clinical substances which are incubated in an environment controlled by the temperature control means;
    means for inverting the operating head after incubation of the clinical substances; and
    means for injecting a washing fluid into the influx chamber of the inverted operating head so that the washing fluid flows upwardly through the prongs and into the receptacles to wash excess of the clinical substances from the solid phase binder, said washing fluid containing said excess draining into the efflux chamber.

2. Apparatus as recited in claim 1 and additionally comprising means for injecting a drying fluid into the influx chamber of the inverted operating head so that the drying fluid flows upwardly through the prongs and into the receptacles to dry the solid phase elements and incubated clinical substances adhering thereto.

3. Apparatus as recited in claim 1 wherein the operating head comprises a base, said temperature control means being located in said base, a rack supporting said upwardly opening receptacles and attachable to said base, and a cover attachable to the base to define said efflux chamber, the influx chamber being located in said cover and the prongs extending from said cover.

4. Apparatus as recited in claim 1 wherein said upwardly opening receptacles comprise individual test tubes.

5. Apparatus as recited in claim 1 wherein the solid phase binder is coated in a bead located in each receptacle, the transverse dimensions of the beads being larger than the annular distance between the prongs and the interior of the receptacles so that the beads are confined in the bottoms of the respective receptacles by the prongs.

6. Apparatus as recited in claim 1 wherein the temperature control means generally surrounds the closed bottoms of the receptacles.

7. Apparatus as recited in claim 1 wherein the temperature control means comprises a heating block.

8. Apparatus as recited in claim 1 and additionally comprising means for rocking the inverted operating head to facilitate incubation of the clinical substances.

9. Apparatus for performing binder-substrate processing of clinical substances comprising:
   an operating head which includes a base, a temperature control means located within said base, means in said base for supporting a plurality of upwardly opening receptacles, and a cover attachable to the base to define an efflux chamber in fluid communication with the receptacles, said cover including an influx chamber and a plurality of prongs extending from the influx chamber into the interior of the receptacles to provide fluid communication between the influx chamber and said receptacles;
   a solid phase binder located at the bottoms of the respective receptacles, said solid phase binder being immersed in said clinical substances which are incubated in an environment controlled by the temperature control means;
   means for inverting the operating head after incubation of the clinical substances;
   means for injecting a washing fluid into the influx chamber of the inverted operating head so that the washing fluid flows upwardly through the prongs and into the receptacles to wash excess of the clinical substances from the solid phase binder, said washing fluid containing said excess draining into the efflux chamber; and
   means for injecting a drying fluid into the influx chamber of the inverted operating head so that the drying fluid flows upwardly through the prongs and into the receptacles to dry the solid phase elements and incubated clinical substances adhering thereto.

10. Apparatus as recited in claim 9 wherein said upwardly opening receptacles comprise individual test tubes.

11. Apparatus as recited in claim 9 wherein the solid phase binder is coated in a bead located in each receptacle, the transverse dimensions of the beads being larger than the annular distance between the prongs and the interior of the receptacles so that the beads are confined in the bottoms of the respective receptacles by the prongs.

12. Apparatus as recited in claim 9 wherein the temperature control means generally surrounds the closed bottoms of the receptacles.

13. Apparatus as recited in claim 9 and additionally comprising means for rocking the inverted operating head to facilitate incubation of the clinical substances.

* * * * *